United States Patent [19]
Huston et al.

[11] Patent Number: 6,087,666
[45] Date of Patent: *Jul. 11, 2000

[54] OPTICALLY STIMULATED LUMINESCENT FIBER OPTIC RADIATION DOSIMETER

[75] Inventors: Alan L. Huston; Brian L. Justus, both of Springfield, Va.

[73] Assignee: The United States of America as represented by the Secretary of the Navy, Washington, D.C.

[*] Notice: This patent is subject to a terminal disclaimer.

[21] Appl. No.: 09/025,033

[22] Filed: Feb. 18, 1998

[51] Int. Cl.[7] .................................. G01T 1/06; G01T 1/10
[52] U.S. Cl. ..................................... 250/484.5; 250/484.4; 250/484.2; 250/361 R
[58] Field of Search .............................. 250/361 R, 362, 250/370.07, 370.11, 484.2, 484.4, 484.3, 484.5, 458.1, 459.1

[56] References Cited

U.S. PATENT DOCUMENTS

| | | |
|---|---|---|
| 4,999,504 | 3/1991 | Braunlich et al. . |
| 5,030,834 | 7/1991 | Lindmayer et al. . |
| 5,091,653 | 2/1992 | Creager et al. ........................ 250/484.5 |
| 5,585,640 | 12/1996 | Huston et al. . |
| 5,606,163 | 2/1997 | Huston et al. . |
| 5,656,815 | 8/1997 | Huston et al. . |
| 5,811,822 | 9/1998 | Huston et al. ........................ 250/484.4 |

*Primary Examiner*—Constantine Hannaher
*Assistant Examiner*—Albert Gagliardi
*Attorney, Agent, or Firm*—Barry A. Edelberg; Ralph T. Webb

[57] ABSTRACT

An optically-stimulated luminescent radiation dosimeter system for the remote monitoring of radiation sources is disclosed. The system includes a radiation-sensitive optically-stimulated dosimeter which utilizes a new, doped glass material disposed at a remote location for storing energy from ionizing radiation when exposed thereto and for releasing the stored energy in the form of optically-stimulated luminescent light at a first wavelength when stimulated by exposure to light energy at a stimulating second wavelength. The system further includes: an optical source for providing stimulating light energy at the stimulating second wavelength; a photodetector for measuring optically-stimulated luminescent emissions; and an optical fiber for passing the stimulating light energy from the optical source to the optically-stimulated luminescent dosimeter to stimulate the optically-stimulated luminescent dosimeter to produce optically-stimulated luminescence light from stored energy and for passing the optically-stimulated luminescence light to the optically-stimulated luminescent detector to enable the photodetector to measure any optically-stimulated luminescent emissions occurring when the optically-stimulated luminescent dosimeter is excited by the light energy at the stimulating second wavelength. Also, the dosimeter can be used for real-time monitoring by detecting the scintillations emitted by the doped glass material upon exposure to ionizing radiation.

20 Claims, 4 Drawing Sheets

OPTICALLY STIMULATED LUMINESCENT FIBER OPTIC RADIATION DOSIMETER

BACKGROUND OF THE INVENTION

1. Field of the Invention

The present invention relates generally to a fiber optic radiation sensor (dose rate meter) and dosimeter and more specifically, to a fiber optic radiation dosimeter for monitoring radiation sources such as ultraviolet, x-ray, gamma radiation, beta radiation, and protons.

2. Description of the Background Art

Thermoluminescent (TL) phosphors have been used for many years to monitor radiation exposure levels. These dosimeters measure the accumulated radiation exposure over a period of time, ranging from minutes, to days to years. Phosphor materials such as metal-ion-activated lithium fluoride (LiF), or calcium fluoride ($CaF_2$) are commonly used in "TLD badges" to monitor personnel exposure to radiation. These dosimeters are generally prepared from powders of the phosphor that are pressed into opaque white pellets. When exposed to ionizing radiation, such as deep ultraviolet, x-ray or gamma radiation, free electrons are generated and are trapped in the material. The electrons remain trapped until a source of heat is applied to the material to stimulate the release of the electrons. The electrons recombine at a luminescence center in the material resulting in the emission of light. The amount of light emitted is proportional to the amount of radiation exposure. TLD phosphors have a number of problems that must be overcome to be used with confidence. TLD phosphors are limited in size because the opacity of the pellet limits the signal to light generated near the surface. As a result, the dimensions of commercial TLD dosimeters are limited, thereby limiting the dynamic range and overall sensitivity of the dosimeter. Although TLD phosphors must be heated in order to function, heating is also the origin of the most significant problems with TLD dosimeters. Heating irreversibly erases the stored information in the dosimeter. Thermoquenching of the signal at elevated temperature reduces the sensitivity. Finally, the sensitivity of the dosimeter changes upon heating such that the sensitivity must be reset before reuse.

Optically stimulated luminescent (OSL) phosphors operate much the same way as TL phosphors except the recombination luminescence is stimulated optically rather than thermally. Thus, OSL dosimeters avoid all of the problems caused by heating in TLD dosimeters. OSL readout of an OSL phosphor typically need not erase all of the stored information, providing the opportunity to perform subsequent OSL or TL readouts of the dose. The sensitivity of OSL dosimeters is not reduced by thermoquenching and it is not changed by the readout since the OSL dosimeter is not heated. Powdered OSL phosphors, however, are still opaque and experience the drawbacks associated with poor optical quality just as in the case of TLD phosphors.

Glasses have been considered previously as potential TLD phosphors since it was recognized that the optical transparency of glass offers the advantage of more efficient light collection. The effectiveness of these glasses for TLD applications has been limited for a number of reasons, including low readout temperatures, low sensitivity compared to crystalline phosphors and low saturation doses. To some extent, these problems were overcome by use of the glasses described in U.S. Pat. No. 5,656,815 to Huston et al, the entirety of which is incorporated by reference herein for all purposes. The glasses described in that patent are highly favorable for TLD dosimetry. U.S. Pat. No. 5,811,822 to Huston et al, issued Sep. 22, 1998 and entitled "OPTICALLY TRANSPARENT, OPTICALLY STIMULABLE GLASS COMPOSITES FOR RADIATION DOSIMETRY" (the entirety of which is incorporated by reference herein for all purposes) describes novel glass phosphor materials that exhibit highly favorable characteristics for OSL dosimetry applications.

Fiber optic coupled remote dosimeters using TLD and OSL phosphors have also been described. One system, described in U.S. Pat. No. 4,999,504, issued Mar. 12, 1991 to Braunlich et al., utilizes powdered TL phosphors attached to the end of a 0.6 mm diameter optical fiber. An absorbing material is applied to one surface of the phosphor and a diode laser is used to heat the absorber which in turn heats the TL material by diffusive heating. This system is described as a remote fiber optic laser TLD system. The performance of the system is limited in several ways. First, the TL material must be very thin, approximately 0.1 mm, to allow the laser heating source to be transmitted through the TL material to the absorber material. As a consequence, in order to attain sufficient TL sensitivity, the diameter of the TL material and the fiber must be fairly large. A similar approach has been described for a fiber optic coupled OSL dosimeter (U.S. Pat. No. 5,030,834, issued Jul. 9,1991, to Lindmayer et al.). In this case, the OSL phosphor powder is attached to the end of a commercial fiber using an epoxy binder. Because of the high degree of scattering in the phosphor powder, only a very thin layer of powder can be used, thereby seriously limiting the sensitivity. U.S. Pat. No. 5,606,163 to Huston et al., the entirety of which is incorporated by reference herein for all purposes, discloses a fiber-optic coupled remote dosimeter that uses a novel laser heated glass fiber dosimeter to accurately measure radiation exposure for doses from ~1 rad to ~8000 rad.

SUMMARY OF THE INVENTION

Accordingly, it is an object of the present invention to provide an optically transparent, optically-stimulable, radiation sensitive, sensor.

It is another object of the invention is to provide an optically transparent, radiation sensitive, scintillating sensor.

It is a further object of the present invention to make a fiberoptic-coupled remote radiation sensor and dosimeter using an optically transparent, optically stimulated or scintillating radiation-sensitive sensor as the detector.

These and additional objects of the invention are accomplished by an optically stimulable fiber-optic-coupled remote dosimeter that uses a glass matrix including luminescent centers and trapping centers. These glass matrices are fully described in the aforementioned U.S. Pat. No. 5,811,822 to Huston et al In these types of glasses, the trapping centers are capable of storing charges (electrons or holes), for example resulting from ionizing radiation, for extended periods of time. The trapped charges may be optically stimulated to recombine by the application of optical energy, resulting in the emission of light energy. This process is known as optically-stimulated luminescence (OSL). In several embodiments, the glass (e.g., fused quartz, fused silica, alumina glass, or borate glass) matrix includes an alkaline earth sulfide doped with an activator/co-activator pair of samarium and another rare earth element. In other alternative embodiments, the glass (e.g., silica, alumina, or borate glass) matrix is doped with ZnS and copper, lead, manganese, or cerium. In yet another embodiment, a glass (e.g., silica, alumina, or borate glass) matrix is doped with Cu or Ce.

Because they are phosphors, the OSL glasses described above also scintillate when exposed to ionizing radiation. This scintillation advantageously permits the present invention to also serve as a real-time monitor of ionizing radiation. Of course, the specific OSL glass used may be selected to maximize scintillation or optically-stimulated luminescence.

In addition to the optically stimulated luminescent glass dosimeter, the present invention also includes an optical source for providing stimulating light energy at a wavelength that stimulates the dosimeter to emit light at an emitted wavelength; a photodetector for measuring luminescent emissions at the emitted wavelength; and an optical fiber for passing the stimulating light energy from the optical source to the optically-stimulated luminescent dosimeter to stimulate the optically-stimulated luminescent dosimeter to produce optically-stimulated luminescence light from stored energy and for passing the optically-stimulated luminescence light to the photodetector to enable the photoluminescent detector to measure any optically-stimulated luminescent emissions occurring when the optically-stimulated luminescent dosimeter is exposed to the stimulating light energy.

BRIEF DESCRIPTION OF THE DRAWINGS

A more complete appreciation of the invention will be readily obtained by reference to the following Description of the Preferred Embodiments and the accompanying drawings in which like numerals in different figures represent the same structures or elements, wherein.

DESCRIPTION OF THE PREFERRED EMBODIMENTS

Figure 1:
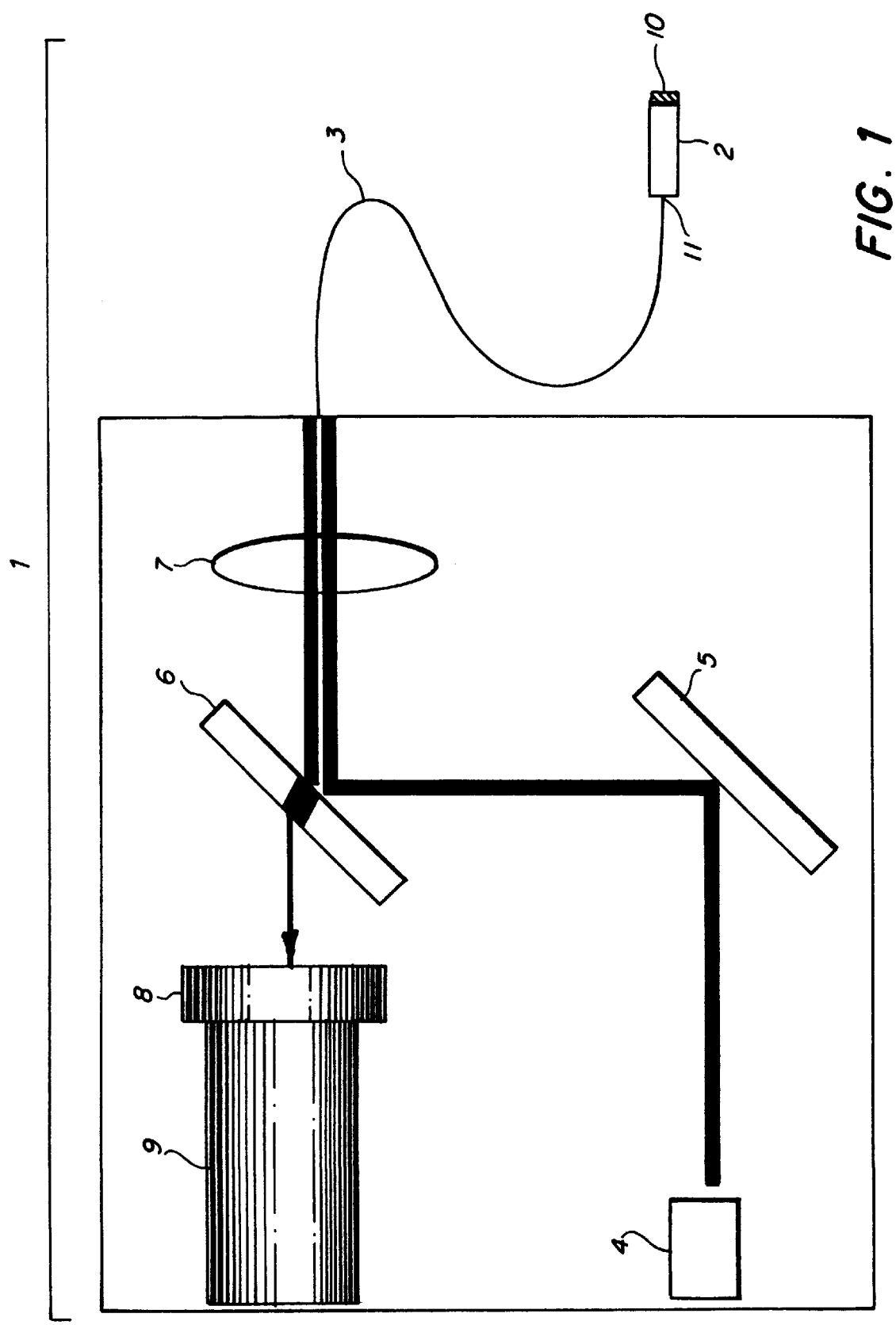
FIG. 1 is a schematic diagram of the optically-stimulated luminescent dosimeter system of the invention.

The optically-stimulated luminescent dosimeter system described in this invention utilizes a novel, semiconductor-and/or metal ion-doped glass material that was recently developed by the present inventors and described in the above-noted U.S. Pat. No. 5,811,822 and in U.S. Pat. No. 5,585,640 to Huston et al., the entirety of which is also incorporated herein by reference for all purposes. Exposure to ionizing radiation, such as deep ultraviolet, x-ray or gamma radiation, results in the formation of trapped electrons in the composite glass material. The electrons remain trapped until the glass material is exposed to light at a stimulating wavelength. Upon exposure to light at a stimulating wavelength, the glass emits a luminescent signal.

In a first embodiment, the doped glass material used in the present invention includes a glass matrix incorporating an alkaline earth sulfide doped with an activator/coactivator pair or with the coactivator alone. The activator/coactivator pair includes samarium and an additional rare earth. The coactivator may be any rare earth, other than samarium, that does not absorb at the stimulating wavelength or the emitted wavelength. Indeed, for the purposes of the present invention, using coactivator alone (i.e., the rare earth other than samarium, e.g., cesium or europium) in glasses of this first embodiment provides results at least equivalent to those achieved by samarium/coactivator pairs. For the purpose of the present invention, the use of samarium alone in glasses of this first embodiment tends to provide inferior results. In a second embodiment, the glass matrix includes ZnS doped with copper, lead, manganese, or cerium. In the first and second embodiments, more than one coactivator may be used. In a third embodiment of the present invention, the glass matrix includes copper and/or cerium, and has either no metal sulfide or a concentration of metal sulfide that is lower than a metal sulfide concentration that significantly alters the luminescent and trapping properties of the glass for its intended purpose. That is, a trace of metal sulfide may be present in the third embodiment, so long as the concentration of the metal sulfide is below that at which the glass begins to noticeably exhibit effects from sulfide doping.

In the first embodiment, any alkaline earth sulfide may be used as the alkaline earth sulfide dopant. Typical alkaline earth sulfides useful in the glass matrix of the present invention include MgS, CaS, SrS, and BaS.

When more than one co-activator is used, the additional coactivator is typically Eu, Ce, or a mixture thereof. Other rare earths should also be useful, in place of or in combination with Eu and/or Ce, as additional co-activators.

The second embodiment of the present invention also employs a sulfide component and an activator. In this second embodiment, however, the metal sulfide component is ZnS, and only a single activator, such as Cu, Pb, Mn, or Ce is required. In a third embodiment of the present invention, the glass matrix includes Cu or Ce dopants in the absence of a metal sulfide component, or even in the absence of any sulfide component. For the purpose of the present specification and claims, a glass is considered essentially free of a component if the glass lacks an amount of that component sufficient to significantly alter the optical stimulability or radiation sensitiveness of the glass.

In each of the embodiments of the present invention, the optically stimulable glasses are typically prepared by diffusing the dopants (including sulfide components) into the glass matrix. Because the dopants are diffused into the glass matrix, the glass matrix may be either porous or fused (non-porous).

The dopants may be diffused into the glass matrix by a wide variety of methods. For example, if the glass matrix is porous, it may be contacted with a solution of salts of the desired dopant metals for a sufficiently long time to diffuse the salts into the porous glass. Thereafter, the porous glass matrix is dried. In those embodiments that include a metal sulfide component that would be insoluble in the dopant solution used, the dopant solution may contain a soluble salt of the metal portion of the sulfide. After drying, the glass may be sulfided (for example by exposure to gaseous $H_2S$ at elevated temperatures, typically about 100° C.) to provide the desired metal sulfide diffused into the porous glass. The porous glass matrix is then consolidated and activated, for example using any of the consolidation and/or activation methods described in Huston et al., supra.

In fused glass, the dopants may be diffused, for example, by dipping the fused glass matrix into an organic-inorganic sol gel (e.g., an organosilicate sol gel) including a salt or salts of the dopant metals. The fused glass matrix is then withdrawn from the sol gel at a slow, steady rate to result in the formation of a porous, thin (typically less than about one micron thick) sol-gel film containing the salt or salts. Upon drying (typically at room temperature to about 200° C.), the organic constituents of the film volatilize and/or decompose, leaving behind a porous, film (a high silica film where an organosilicate sol-gel was used) containing the salts. The glass having the porous film thereon may be sulfided (for example by exposure to gaseous $H_2S$ at elevated temperatures, typically about 100° C.) to provide metal sulfides, if desired. The resulting material is then activated, typically after being placed within a glass (e.g., silica) tube that is then placed within a tube furnace. If sulfiding is not desired, the decomposition and activation steps may be combined, for example, by heating the sol-gel film to a sufficiently high temperature to decompose the organics and diffuse the resulting metal(s) into the glass and activate them. Appropriate conditions for activation are the same as those described for the activation of porous glasses. Of course, the fused glasses made according to the present invention do not require consolidation. Porous glass matrices may also be doped using this sol gel method.

After several doping operations have been performed, the fused glass tube used to hold the glass samples during activation becomes a source of metal ion dopants. Untreated glass (fused or porous) may then be doped and activated by heating to activation temperatures of typically over 1000° C. while inside the previously used glass tube. This effect apparently results from a "seasoning" of the glass with small amounts of the dopant metal ions. During heat treatment, a low vapor pressure of the metal dopant atoms or ions is created that bathes the undoped glass in a doping atmosphere. The metal doping elements diffuse into the fused or porous glass material. Even where the source glass includes metal sulfides, only the metal ions will dope the glass to a significant extent. The concentration of sulfide in the doped glass will be below that at which effects from sulfide doping become apparent. Thus, the resulting glass is essentially sulfide free. The OSL activity of fused glasses may be achieved by repeated heat treatments in the presence of unconsolidated metal sulfide-containing pieces of Vycor™ or other porous glass.

As should be apparent from the above description of doping untreated glasses by heat treatment within a "seasoned" fused glass (e.g., silica, alumina, or borate) tube, the dopants need be present in only minute amounts within the glass to cause significant and useful OSL activity. Thus, it is extremely difficult to quantitatively define a minimum dopant level required to obtain useful OSL properties. The maximum doping level is that at which either the dopants within the glass matrix obtain crystallite sizes sufficiently large to significantly increase scattering, or the OSL effect is significantly attenuated by a self-quenching mechanism.

The dopant salts used in the solutions and sol gels discussed above are typically selected so that the salt is soluble in the solution or sol gel and the anion component of the salt, upon reduction, forms a gas or mixture of gases that are non-reactive, or beneficially reactive, with the doped glass matrix. The concentrations of these salts in the sol gels and solutions may vary widely. For example, each salt is typically present at a concentration of about 0.001 g per 100 ml solution up to its saturation point at the temperature at which the glass matrix is contacted with the solution or sol gel.

The glass matrix provides a mechanically robust, chemically inert phosphor material that is fully compatible with high quality, commercial optical fibers. The material withstands cycling through temperature extremes of up to 1200° C., without any apparent loss in performance. The glass matrix may be doped in bulk form or may be doped in the form of powders or fibers (e.g., glass wool). Also, if desired, a doped bulk glass matrix may be powdered or drawn into fibers.

The optical transparency of the glass provides for applications that are not possible using traditional powder phosphors. Optically transparent OSL glass dosimeters allow for efficient detection of radioactive particles such as $\alpha$, $\beta$ and tritium. These particles do not penetrate deeply into the material, but the waveguiding property of the glass provides for efficient detection. The OSL readout process is much faster than thermal readout methods, making possible much faster processing.

The exemplary Cu-doped glass material absorbs ultraviolet light at about 266 nanometers (nm) and emits optically-stimulated luminescence in a broad band ranging from about 400 nm to about 620 nm and has a peak intensity at about 500 nm (with a color that appears to be blue-green). Unlike the thermoluminescent glass dosimeter used in the aforementioned U.S. Pat. No. 5,606,163, the glass used in the dosimeter system of the present invention is not heated and the OSL system is not reliant on heating for its operation. The glass is essentially free of rare earth dopants (such as $Nd^{3+}$) that absorb a significant fraction of the stimulation light. Trap release is not stimulated thermally by the absorption of light energy. In addition, the OSL signal is not attenuated due to absorption in the blue-green wavelength range by a rare earth ion dopant, as occurs in the invention described in the aforementioned U.S. Pat. No. 5,606,163. In the glass used in the present invention, recombination of trapped electrons results from direct optical stimulation of the trapped electrons, rather than optically induced heating.

A disadvantage in using the laser heated glass is the Nd ions absorb both the stmulation light from the optical source and the thermoluminescence signal light, thereby limiting the length of the sensor element that can be used. This problem in turn limits the sensitivity of the dosimeter. In an OSL dosimeter, an almost unlimited length of OSL glass dosimeter can be used to increase the sensitivity of the system, since the stimulation light from the optical source is absorbed only by radiation populated traps in the glass. These traps are in turn depopulated and no longer absorb the optical source light. Another advantage of the present invention is that it is much faster than the laser-heated TLD approach. Also, the OSL method does not suffer from thermal quenching of the signal as occurs in laser-TLD. There is no heating at all using the OSL approach. Thus, in in vivo applications, there will be no harmful effects due to even modest heating as might be expected for the laser-heated TLD.

The basic dosimetry system in which this novel glass is employed is described in the aforementioned U.S. Pat. No. 5,606,163. The present invention, however, uses the novel optically transparent, optically stimulable luminescent glass described above in place of the laser heated thermoluminescent glass used in that patent. In addition, the present invention includes an alternative dosimetry method using the scintillation light from the fiber-optic coupled OSL. This alternative dosimetry method, which provides a real-time readout, was not practical using the previously disclosed laser heated dosimeters.

FIG. 1 shows a schematic diagram of the Optically-Stimulated Luminescent Fiber Optic Radiation Dosimeter system 1 of this invention. The optically-stimulated luminescent fiber optic radiation dosimeter system 1 includes a remotely positioned, optically transparent, optically stimulated luminescent glass dosimeter 2 attached to an optical fiber or fiberoptic cable 3. The optically-stimulated luminescent fiber optic radiation dosimeter system 1 also includes an optical source 4 a turning mirror 5, a dichroic beamsplitter 6, a focussing lens 7, an optical filter 8, and a photodetector 9. It should be understood that a fiber splitter or optical coupler can be used in place of the dichroic beamsplitter 6.

The optically-transparent, optically-stimulated luminescent (OSL) glass dosimeter 2 contains the optically-stimulated luminescent glass dosimeter material described above.

The material of the optically-stimulated luminescent (OSL) dosimeter 2 may be in the form of a rod, fiber, plate or tube. An end of the glass dosimeter 2 may contain an optional broadband reflective coating 10.

In the operation of the optically-stimulated luminescent dosimeter system 1 of FIG. 1, about 0.8 micrometer ($\mu$m) to about 10 micrometer ($\mu$m) (typically about 0.8 micrometer ($\mu$m) to about 1.2 micrometer ($\mu$m)) light from the optical source 4 (which may be, for example, a diode laser in the range of 0.8 micrometer ($\mu$m) to 10 micrometer ($\mu$m) (typically about 0.8 micrometer ($\mu$m) to about 1.2 micrometer ($\mu$m)), a gas laser, a molecular laser, a solid state laser, or a lamp) and at an exemplary 800 nanometer (nm) wavelength is reflected by the dichroic beam splitter 6 and focused by the lens 7 into the optical fiber or fiberoptic cable 3 which may be, for example, several kilometers in length. The optical fiber 3 is fused at its far end 11 to the dosimeter glass material of the optically-stimulated luminescent dosimeter 2 so that the dosimeter glass material effectively becomes a part of the optical fiber 3. Thus, the optical fiber 3 directs light energy from the light source 4 to the optically stimulated luminescent material in the OSL dosimeter 2. It is preferable that the OSL glass dosimeter 2 and the optical fiber 3 have substantia lly identical end face configurations at the far end 11 of the optical fiber 3 to maximize the transfer of light energy from the optical fiber 27 into the OSL glass dosimeter 2. The light entering the OSL glass dosimeter 2 stimulates emission of light at a different wavelength to be detected by the photodetector 9.

Optical source 4 can be any type of light source (such as the previously-mentioned exemplary diode laser, molecular laser, solid state laser, or lamp) that can provide light energy at an appropriate light wavelength sufficient to excite the OSL glass material in the OSL glass dosimeter 2 to produce OSL emissions.

The blue-green, 500 nm (in the case of the exemplary Cu-doped glass) optically-stimulated luminescent light in the dosimeter 2 is directed back through the optical fiber 3, collimated by the lens 7 and passed through the dichroic beam splitter 6. When the optional broadband reflective coating 10 is disposed at an end of the glass dosimeter 2, the reflective coating 10 will minimize any loss of optically-stimulated luminescence or scintillation signal light out of the far end of the dosimeter 2 by reflecting it back to the optical fiber 3, and even more signal light will be directed back to the photodetector 9. The stimulating light will also be reflected by the reflective coating, effectively using the pump light twice.

The dichroic beam splitter 6 is designed to transmit the visible 500 nm signal therethrough and reflect the 800 nm light from the optical source 4. The transmitted 500 nm OSL light is filtered by the filter 8 to remove background light (stray light from the optical source) and is detected by the photodetector 9 which is sensitive to light in the range from about 450 nm to about 850 nm. The photodetector 9, which may be a photomultiplier tube, a photodiode or any other suitable photodetector, measures the optically-stimulated luminescent emissions from the OSL glass dosimeter 2.

Optically-stimulated remote dosimetry systems according to the present invention have a variety of applications. These applications, of course, include the same application as described in U.S. Pat. No. 5,606,163.

Figure 2:
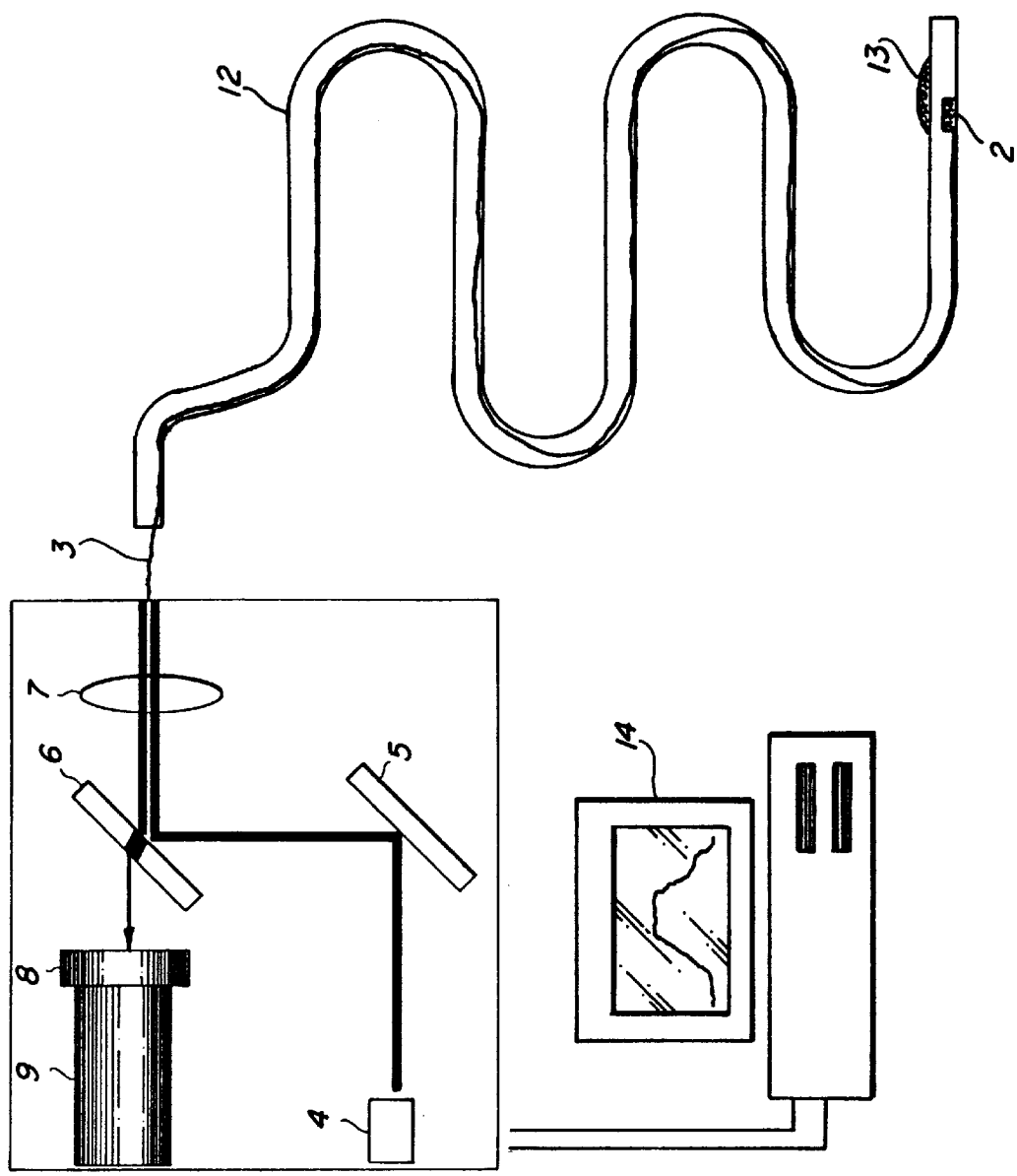
FIG. 2 is a first exemplary application of the optically-stimulated luminescent dosimeter system of the invention in the monitoring of nuclear contamination in pipes at a nuclear processing facility.

FIG. 2 illustrates a first exemplary application of the optically-stimulated luminescent dosimeter system of the invention in the monitoring of nuclear contamination in a drain pipe at a nuclear processing facility. Monitoring for contamination in nuclear facilities is an important problem. The OSL glass dosimeter 2 of FIG. 1 is capable of withstanding harsh environments. As shown in FIG. 2, a dosimeter 2 could be could be snaked through a drainage pipe 12 at a nuclear processsing facility to remotely characterize and survey contamination in the pipe. Accurate survey of such contamination in drainliners will significantly reduce the costs and risks associated with remediation as part of the process of decontamination and decomissioning.

The fiberoptic-coupled OSL radiation sensor system 1 is used to detect radioactive contamination in the pipe system as the dosimeter 2 is slowly withdrawn from the pipe 12. Accumulations of radioactive waste 13 at certain locations inside the pipe 12 produce higher OSL or scintillation signal levels in the dosimeter 2 and are detected with the sensor system 1 and displayed on a computer screen 14. By precisely locating the radioactive contamination 13 inside the pipe 12, and removing small sections of the pipe 12 for special processing will greatly reduce the costs of decomissioning former nuclear processing facilities.

The small size of the fiberoptic coupled radiation dosimeter 2 and the flexible nature of the fiberoptic cable 3 allow this sensor to be deployed inside small diameter pipe systems 12. The remote operation of the sensor system 1 provides for improved safety for nuclear clean-up technicians.

Figure 3:
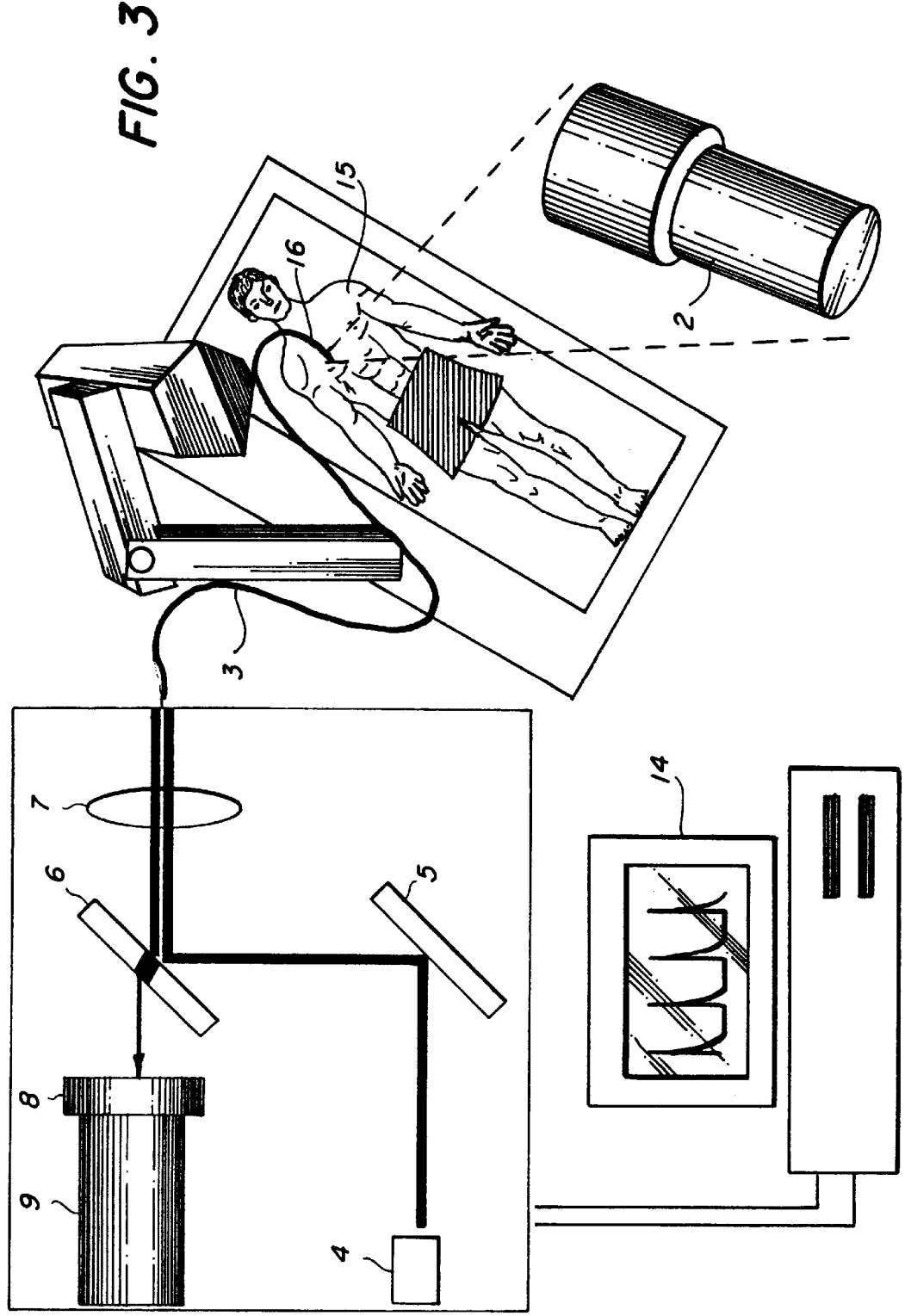
FIG. 3 is a second exemplary application of the optically-stimulated luminescent dosimeter system of the invention for in vivo radiation monitoring of radiation doses in patients undergoing radiation therapy.

FIG. 3 illustrates a second exemplary application of the optically-stimulated luminescent dosimeter system of the invention for in vivo radiation monitoring of radiation doses in a patient 15 undergoing radiation therapy.

Monitoring of radiation doses in a patient 15 undergoing radiation therapy can help to improve the effectiveness of radiation treatments. In this application of the optically-stimulated luminescent dosimeter system 1 of the invention, the fiberoptic-coupled, optically stimulated luminescent dosimeter 2 is used in conjunction with a fiber catheter 16 to introduce the dosimeter inside the body of a human patient 15. In this manner, the optically-stimulated luminescent dosimeter 2 can be directed to a certain portion of the human body that is being exposed to radiation as, for example, in radiation therapy for cancer treatment. The dosimeter 2 can be placed next to a tumor that is being irradiated and provide the physician with an immediate feedback as to how much of a radiation dose that he is applying to the tumor during radiation therapy. The radiation dose can be read out while the radiation exposure is in progress or after the exposure has ceased. This would allow more precise control of radiation doses and help reduce collateral damage to healthy tissues.

The optically-stimulated luminescent dosimeter system described above is an all-optical radiation sensing system. The optically-stimulated luminescent glass material in the dosimeter system is sensitive to ionizing radiation. The readout of the material is optically stimulated by an extremely small absorption of semiconductor laser light. The laser light is directed to the OSL material by way of a fiberoptic cable. The OSL material is transparent to the OSL emission wavelengths (420 nm–550 nm) and this light is directed back to a detector by way of the same fiberoptic cable. The readout of the material is also achieved by measuring the scintillation from the material during radiation exposure.

The optically-stimulated luminescent dosimeter system offers fast, in-situ readout. The glass dosimeter material does not have to be placed in a separate OSL machine for analysis.

The dosimeter material is optically transparent to the OSL emission wavelengths. The glass dosimeter material can be any arbitrary size or shape, thus increasing the sensitivity of the OSL glass dosimeter.

The OSL dosimeter system is fiberoptic coupled.

The OSL dosimeter system can be operated by remote control, thus minimizing the exposure of workers to radiation sources.

The OSL glass dosimeter of the OSL dosimeter system can be placed in severe environments and will withstand temperatures in excess of 800 degrees C. The OSL glass dosimeter is not moisture sensitive and can withstand corrosive environments.

The OSL glass dosimeter material is inexpensive, easy to synthesize and achieves reproducible performance.

Having described the invention, the following examples are given to illustrate specific applications of the invention including the best mode now known to perform the invention. These specific examples are not intended to limit the scope of the invention described in this application.

EXAMPLES

A radiation sensitive glass sensing element was fabricated from a 1 mm long, 0.4 mm diameter fused quartz fiber that was doped with $Cu^{+1}$ ions. This small piece of doped fiber was attached to the distal end of a 10 m long, 0.4 mm core diameter commercial optical fiber to yield the fiberoptic-coupled dosimeter used in this work. Typically, 0.1 W of 790 nm light from a solid state diode laser was injected into the fiberoptic-coupled dosimeter to stimulate the release of charges that had been trapped by prior exposure to ionizing radiation. A fraction of the 500 nm OSL signal light, generated by the radiative recombination of the released charges, was directed by total internal reflection back through the fiber, collimated with a lens, transmitted through a dichroic beamsplitter and detected with a photomultiplier tube. Color glass filters were used to isolate the blue-green OSL signal light from the near infrared stimulation light.

Experiments were conducted using radiation from a Varian Clinac 20 (15 MV) beam therapy machine. This machine provided radiation at dose rates variable from 100 cGy/min up to 500 cGy/min. The total dose could be set from 1 cGy to 999 cGy. All of the experiments were performed using a solid water phantom and each dose was calibrated using a microionization chamber at a reference position inside the phantom directly below the fiberoptic dosimeter.

Figure 4:
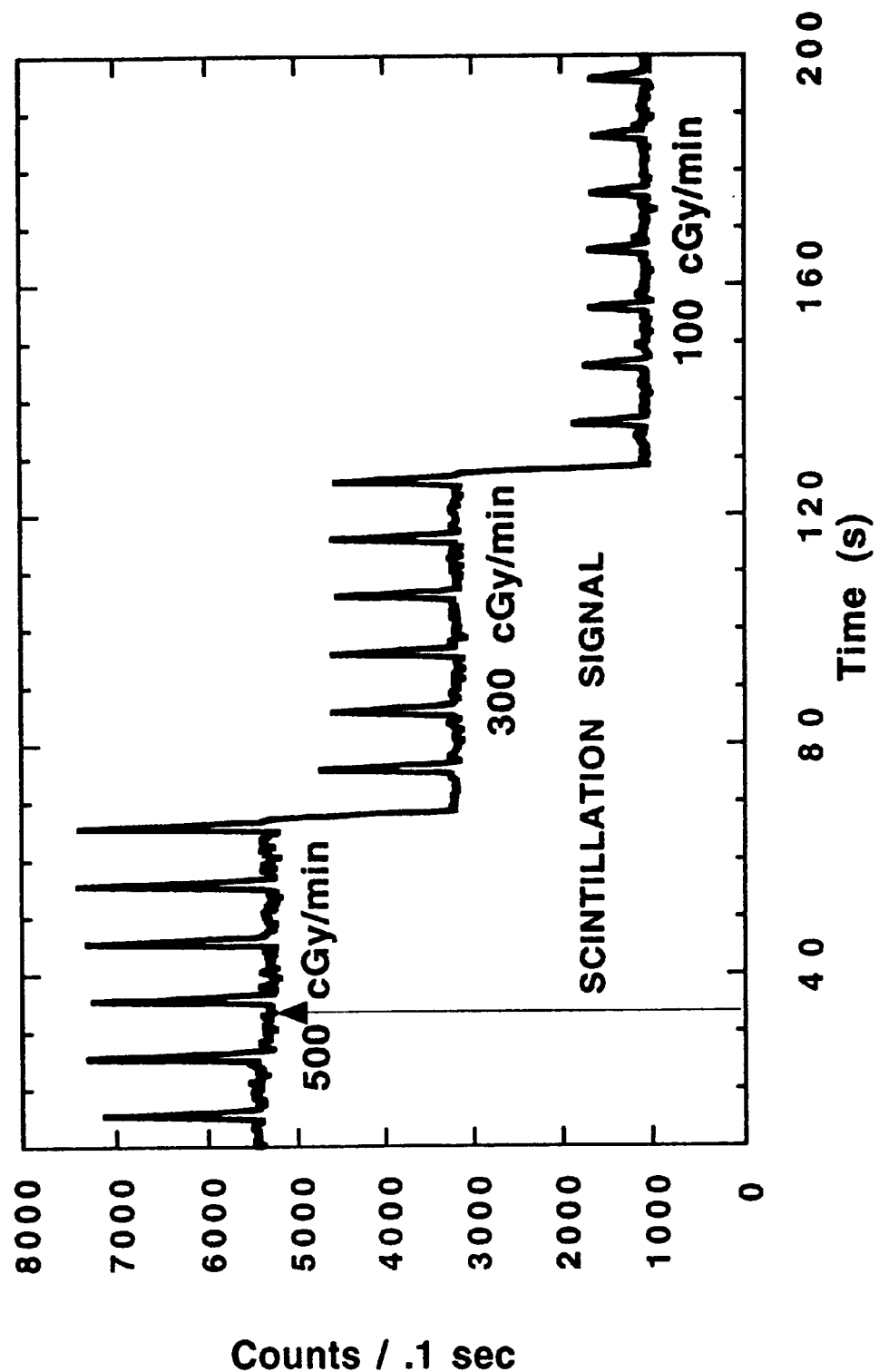
FIG. 4 shows a signal recorded using the fiber-optic coupled OSL dosimeter of the present invention.

FIG. 4 shows a real-time plot of the response of the dosimeter as the dose rate of the Clinac 20 was varied from 500 cGy/min to 300 cGy/min to 100 cGy/min. The periodic spikes represent a series of 1 second duration OSL readouts performed every 10 seconds during the exposure. The elevated baselines are due to the prompt scintillation signal from the radiation sensitive glass. The integrated area under each successive OSL peak provides the dose rate in terms of dose per integration period. The integrated signals from a series of OSL measurements obtained every 10 seconds over a 3 minute time span were constant to within 2% from start to finish. The total accumulated dose can be obtained by summing the individual 10 second dose increments.

Obviously, many modifications and variations of the present invention are possible in light of the above teachings. It is therefore to be understood that, within the scope of the appended claims, the invention may be practiced otherwise than as specifically described.

What is claimed is:

1. An optically-stimulated luminescent radiation dosimeter system for the remote monitoring of a radiation source, said system comprising:

a radiation-sensitive optically-stimulated luminescent dosimeter for storing energy from ionizing radiation when exposed thereto and for releasing the stored energy in the form of optically-stimulated luminescence light at a first wavelength when stimulated by exposure to light energy at a stimulating second wavelength, said optically stimulated luminescent dosimeter including an optically stimulable glass matrix material that stores energy in the form of trapped electrons when exposed to ionizing radiation, said optically stimulable glass including luminescence centers that upon exposure to light at said second wavelength, recombine with said trapped electrons, resulting in the release of said stored energy at said first wavelength; said glass being transparent to its optically stimulated emissions;

a photodetector for measuring optically-stimulated luminescent emissions at the first wavelength; and an optical fiber for directing the stimulating light energy to said optically-stimulated luminescent dosimeter to stimulate said optically-stimulated luminescent dosimeter to produce optically-stimulated luminescence light from stored energy and for passing the optically-stimulated luminescence light to said photodetector to enable said photodetector to measure any optically-stimulated luminescent emissions occurring when the optically-stimulated luminescent dosimeter is stimulated by the light energy at the stimulating second wavelength, wherein the optically-stimulated luminescent dosimeter is fused to the optical fiber.

2. The optically-stimulated luminescent radiation dosimeter system of claim 1, further comprising an optical source for providing stimulating light energy at the stimulating second wavelength, and wherein said optical fiber directs the stimulating light energy from said optical source to said optically-stimulated luminescent dosimeter.

3. The optically-stimulated luminescent radiation dosimeter system of claim 2 wherein:

said optical source is selected from the group consisting of a diode laser, a molecular laser and a solid state laser.

4. The optically-stimulated luminescent radiation dosimeter system of claim 2 wherein:

said optical source is selected from the group consisting of a discharge lamp, and incandescent lamp, and a light emitting diode.

5. The optically-stimulated luminescent radiation dosimeter system of claim 1, wherein said optically-stimulable glass comprises a glass matrix doped with an amount of Cu ions sufficient to provide said glass with optically stimulable luminescence.

6. The optically-stimulated luminescent radiation dosimeter system of claim 5, wherein said glass is essentially free of metal sulfides.

7. The optically-stimulated luminescent radiation dosimeter system of claim 1, wherein said glass is essentially free of rare earth dopants that absorb a significant fraction of the excitation wavelength and re-emit that absorbed energy as thermal energy that detraps trapped electrons.

8. The optically-stimulated luminescent radiation dosimeter system of claim 7, wherein said optically-stimulable glass comprises a glass matrix doped with an amount of Cu ions sufficient to provide said glass with optically stimulable luminescence.

9. The optically-stimulated luminescent radiation dosimeter system of claim 8, wherein said glass is essentially free of metal sulfides.

10. The optically-stimulated luminescent radiation dosimeter system of claim 1, wherein said glass is a glass matrix doped with an alkaline earth sulfide and an additional dopant selected from the group consisting of Eu ions and Ce ions, said alkaline earth sulfide and said additional dopants being present in amounts sufficient to provide said glass with optically stimulable luminescence.

11. The optically-stimulated luminescent radiation dosimeter system of claim 1, wherein said glass is a glass matrix doped with ZnS and an additional dopant selected from the group consisting of Pb ions, Cu ions, and Mn ions, said ZnS and said additional dopant being present in an amount sufficient to provide said glass with optically stimulable luminescence.

12. A method of monitoring, from a remote location, a source of ionizing radiation, said method comprising the steps of:

exposing to ionizing radiation a radiation-sensitive optically-stimulated luminescent dosimeter for storing energy from ionizing radiation when exposed thereto and for releasing the stored energy in the form of optically-stimulated luminescence light at a first wavelength when stimulated by exposure to light energy at a stimulating second wavelength, said optically stimulated luminescent dosimeter including an optically stimulable glass matrix material that stores energy in the form of trapped electrons when exposed to ionizing radiation, said optically stimulable glass including luminescence centers that upon exposure to light at said second wavelength, recombine with said trapped electrons, resulting in the release of said stored energy at said first wavelength; said glass being transparent to its optically stimulated emissions;

an optical source for providing stimulating light energy at the stimulating second wavelength;

a photodetector for measuring optically-stimulated luminescent emissions at the first wavelength; and passing said stimulating light energy from said optical source to said optically stimulated luminescent dosimeter through an optical fiber fused to the optically-stimulated luminescent dosimeter, thereby stimulating said optically-stimulated luminescent dosimeter to produce optically-stimulated luminescence light from stored energy conveying said optically-stimulated luminescence light to said photodetector, through an optical fiber, to enable said photodetector to measure any optically-stimulated luminescent emissions occurring when the optically-stimulated luminescent dosimeter is stimulated by the light energy at the stimulating second wavelength, said photodetector providing, at said location remote from said source of ionizing radiation, a signal indicative of the amount of ionizing radiation at the location of said source of ionizing radiation.

13. The method of claim 12, wherein said optical source is selected from the group consisting of a diode laser, a molecular laser and a solid state laser.

14. The method of claim 12, wherein said optical source is selected from the group consisting of a discharge lamp, an incandescent lamp, and a light emitting diode.

15. The method of claim 12, wherein said optically-stimulable glass comprises a glass matrix doped with an amount of Cu ions sufficient to provide said glass with optically stimulable luminescence.

16. The method of claim 15, wherein said glass is essentially free of metal sulfides.

17. The method of claim 12, wherein said glass is essentially free of rare earth dopants that absorb a significant fraction of the excitation wavelength and re-emit that absorbed energy as thermal energy that detraps trapped electrons.

18. The method of claim 12, wherein said glass is a glass matrix doped with an alkaline earth sulfide and an additional dopant selected from the group consisting of Eu ions and Ce ions, said alkaline earth sulfide and said additional dopants being present in amounts sufficient to provide said glass with optically stimulable luminescence.

19. The method of claim 12, wherein said exposing step causes said glass to scintillate, and further comprising the step of detecting said scintillation.

20. A method of monitoring a source of ionizing radiation, said method comprising the steps of:

exposing to ionizing radiation a radiation-sensitive optically-stimulated luminescent dosimeter, said optically stimulated luminescent dosimeter including an optically stimulable glass matrix material that scintillates upon exposure to ionizing radiation and that stores energy in the form of trapped electrons when exposed to ionizing radiation, said optically stimulable glass including luminescence centers that upon exposure to light at a second wavelength, recombine with said trapped electrons, resulting in the release of said stored energy as optically stimulated luminescent transmissions at a first wavelength; said glass being transparent to said optically stimulated emissions;

conveying the resultant scintillation light to a photodetector to enable said photodetector to measure said scintillation occurring when the dosimeter is exposed to ionizing radiation, said photodetector providing a signal indicative of the amount of ionizing radiation from said source of ionizing radiation.

* * * * *